United States Patent [19]

Avrameas et al.

[11] Patent Number: 4,925,921

[45] Date of Patent: * May 15, 1990

[54] PRODUCTS OF COUPLING BIOLOGICAL SUBSTANCES BY COVALENT BONDS

[75] Inventors: Stratis Avrameas, Saint Cloud; Thérèse M. F. Ternynck, Paris, both of France

[73] Assignee: Etablissement Declare d'Utilite Publique Dit. Institut Pasteur, Paris, France

[*] Notice: The portion of the term of this patent subsequent to Mar. 18, 1997 has been disclaimed.

[21] Appl. No.: 843,324

[22] Filed: Mar. 24, 1986

Related U.S. Application Data

[60] Division of Ser. No. 561,629, Dec. 15, 1983, which is a continuation of Ser. No. 250,368, Apr. 2, 1981, abandoned, which is a continuation of Ser. No. 79,929, Sep. 28, 1979, abandoned, which is a division of Ser. No. 746,552, Dec. 1, 1976, Pat. No. 4,193,982.

[30] Foreign Application Priority Data

Dec. 5, 1975 [FR] France ................... 75 37392

[51] Int. Cl.⁵ ................. C08G 83/00; C07K 1/10; C07H 21/00; C12Q 1/68
[52] U.S. Cl. ................... 530/389; 530/388; 530/395; 530/406; 530/410; 536/27; 435/6; 436/501
[58] Field of Search .......... 530/388, 389, 395, 406, 530/410; 536/27; 435/6; 436/501

[56] References Cited

U.S. PATENT DOCUMENTS

3,322,634  5/1967  Fulthorpe ................. 436/818 X
4,193,982  3/1980  Avrameas et al. ........... 436/522 X
4,592,998  6/1986  Avrameas et al. ........... 436/520 X

OTHER PUBLICATIONS

Immunochemistry, 1974, vol. 11, pp. 261–269, Lemieux et al.
Immunochemistry, 1977, vol. 14, pp. 767–774, Ternynck et al.
Ann. Immunol (Inst. Pasteur), 1976, 127 C, 197–208, Ternynck et al.
EMBO Journal, vol. 2, No. 10, pp. 1655–1663, 1983, Louvard et al.
Joel W. Goodman, PhD, & An-Chuan Wang, Phd, "Basic & Clinical Immunology", second edition, pp. 23–24, Immunoglobulins: Structure & Diversity, Lange Medical Publications, Los Altos, California.
Brandt, J. et al, *Biochim. Biophys. Acta*, vol. 386, 1975, pp. 196–202.
Morrison, M. et al., *Archiv. Biochem. Biophys.*, vol. 134, 1969, pp. 515–523.

*Primary Examiner*—Herbert J. Lilling
*Assistant Examiner*—Stephanie N. Zitomer
*Attorney, Agent, or Firm*—Sprung Horn Kramer & Woods

[57] ABSTRACT

This process involves the use of benzoquinone as crosslinking agent in large excess compared with the substance to be activated. The activation reaction is realized in a homogeneous liquid medium. Said process making it possible for example to couple antibodies to enzymes for determining or detecting said antibodies.

The process can be used for the determination of antitetanic antibodies in human serum.

1 Claim, No Drawings

PRODUCTS OF COUPLING BIOLOGICAL SUBSTANCES BY COVALENT BONDS

This is a division of application Ser. No. 561,629, filed December 15, 1983, now pending, which is a continuation of application Ser. No. 250,368, filed April 2, 1981, now abandoned, which was a continuation of application Ser. No. 079,929, filed September 28, 1979, now abandoned, which was a division of application Ser. No. 746,552, filed December 1, 1976, which is now U.S. Pat. No. 4,193,982.

The present invention relates to the field of coupling biological substances such as proteins, glycoproteins, polysaccharides, nucleic acids, red blood cells and other biological substances capable of being coupled by means of covalent bonds. The object of the invention is more precisely a process for coupling macromolecules with one another or with red blood cells by covalent bonds.

The coupling of two proteins has already been effected as, for example, in the case of an antibody and an enzyme, with a preferentially difunctional coupling agent such as glutaraldehyde. It is also known how to obtain a covalent bond between a hormone such as progesterone and an enzyme such as β-D-galactosidase using carbodiimide.

Such reactions have notably been described in French Patents 74.19.100 and 74.34.529. Other relevant bibliographical references will be discussed hereinafter.

The choice of coupling agents is essential, as it conditions both the yield of the reaction and also the activity of the biological substances, particularly proteins when, for example, these are enzymes, antibodies, or other similar proteins substances.

It would therefore be desirable to possess a coupling agent making it possible to simultaneously obtain high coupling yields while retaining a large proportion of the biological activity of the macromolecules.

A new process has now been found for coupling at least two biological substances with one another by covalent bonds by means of a bridging or cross-linking agent, said agent being benzoquinone.

The process of the invention comprises the steps of:

(a) treatment of the first substance by a large excess of benzoquinone, said reaction, referred to as the activation reaction, being effected in a homogenous liquid medium;

(b) removal of the reaction products of step (a) and the excess benzoquinone and recovery of the activated substance;

(c) contacting the activated substance with the second substance to be coupled.

According to a basic feature of the new process, the activation treatment of step (a) is realized in solution. This is particularly the case when an "activated" protein is to be coupled with another protein or a particular substance such as red blood cells.

Step (a) of the process is effected by contacting the first substance such as a protein dissolved in a suitable medium with benzoquinone in solution.

As a solvent medium any organic water-miscible solvent or mixture of solvents in which benzoquinone is soluble may be used. Buffered aqueous media are used wherein the first substance such as a protein is soluble. Said media are well known to those skilled in the art. According to the invention media are selected having a pH in the range of about 5.5 to about 9, preferably a pH of about 6–6.2.

A suitable solvent medium for benzoquinone is a lower aliphatic alcohol such as ethanol.

Generally speaking, the invention provides for coupling substances certain of which are capable of being put in solution in an organic water-miscible solvent medium, thus making it possible to realize the activation of step (a) in solution. Thus, in the case of proteins, it is advantageous to treat them with benzoquinone in solution to avoid irreversible insolubilization of the protein.

The reaction with benzoquinone is effected at a temperature preferably not higher than 22° C. until the coupling agent is attached to the substance to be activated, such as the protein, for example for a period of from a few minutes to 24 hours and notably of about half an hour.

During the benzoquinone activation reaction it is advisable to use a large excess of the coupling agent based on the substance to be activated such as the protein. The excess of benzoquinone is defined by the ratio of the number of molecules of the reagent (benzoquinone) to the number of molecules of the substance to be activated.

The amount of excess benzoquinone is a critical factor of the present invention. With values which are too low activation is nil or very slight, and is then insufficient to permit coupling. It is therefore advantageous to use very large excesses of benzoquinone which promote the activation reaction. Expressed in moles, the values of the excess of benzoquinone with respect to the substance to be activated, such as a protein, are at least 200, for example higher than equal to 1000. A suitable practical value is $2.5 \times 10^3$.

Removal of the reaction products and excess benzoquinone can be realized, for example, by passing the substance through a molecular filtration column such as that available on the market under the name "Sephadex".

According to the invention the substance, "activated" after reaction with benzoquinone, can be coupled with another biological substance in order to obtain coupling of the two substances by covalent bonds. The mode of procedure for effecting such coupling is relatively critical. The operation is generally carried out at a temperature of less than 22° C., or preferably at 4° C. The satisfactory period is of 24 hours at 22° C. and 48 hours at 4° C. Coupling is advantageously realized in a medium which is a mutual solvent of the substances, if they are soluble as is the case of proteins, in a buffer medium. The coupling necessitates a pH slightly alkaline between 8 and 9, and the presence of carbonate ions is preferable. The operation is generally conducted with an excess of labelling substances with respect to the other substance. It is possible to obtain coupling with equimolar proportions of the substances to be coupled.

However, according to circumstances, it is possible to use an excess of substance treated with benzoquinone compared with the substance to be coupled, or an excess of the untreated substance to be coupled compared with the benzoquinone-treated substance. Therefore, depending on the case, the variations in amounts are in the range of from 1 to 4 (relations expressed in moles).

The process of the present invention is particularly suitable when one of the proteins is an antibody and the other protein is an enzyme.

As benzoquinone derivatives exist currently in the ortho and para forms either one or another isomer or a mixture thereof may be used. It is, however, preferable to react the parabenzoquinone.

This agent is interesting because it is possible to control its reaction with the macromolecules. At pH 6, the benzoquinone fixes on the protein molecules forming then monosubstituted derivatives and the operation must be then effected at an alkaline pH to make possible the second reaction either at another molecule of the same protein with formation of polymers, or at another molecule of another protein with formation of conjugates. Therefore benzoquinone can be used in two steps coupling reactions which are perfectly controllable.

It was found that the original use of this quinone made it possible to obtain high coupling yields superior than 30% which could be as great as 65% or more according to the proteins used.

As has already been stated, the process of the invention can be used to couple antibodies to enzymes, such couplings can be used to detect or determine antibodies and antigens.

Said process also permits the coupling of macromolecules and red blood cells, as the use of benzoquinone as a cross-linking agent makes it possible to effect reactions whose sensitivity is substantially greater than the previously obtained with others bondings agents such as glutaraldehyde.

A man of the art will understand that the process of the present invention may be used to couple two or more macromolecules or mixture of macromolecules.

Without wishing to tie ourselves down to a particular theory, it is assumed that the remarkable results obtained with the process of the invention are due to the fact that benzoquinone can react with groups other than the amino groupings for which many reagents are already used: glutaraldehyde, carbodimides, diisothiocyanates, bis-diazobenzidine, etc.. Said quinone reacts with oside groups without impairing the antigenic determinants of said molecules.

The article by Martin MORRISON et al [Archives of Biochemistry and Biophysics, 134, 515–523, (1969)] bearing the title "The reaction of benzoquinone with amines and proteins" shows that benzoquinone reacts with aminoacids under very gentle conditions. Benzoquinone can thus provide addition products with proteins with the formation of high energy covalent bonds. The authors of this article have, for example, studied the fixing of benzoquinone on cytochrome c and have shown that the resulting reaction products are capable of catalyzing the oxidation of ascorbates, which may be advantageous in the study of biological systems.

It should first be noted that the said article in no way suggests a coupling of various proteins with benzoquinone. Its teaching is limited to an addition reaction of benzoquinone with a protein and, therefore, the reaction conditions described in the Martin Morrison Article are such that they permit a simple addition of benzoquinone to the protein (cytochrome c); in particular the molar excess of benzoquinone with respect to the protein is a maximum of 10:1. Thus during the reaction of benzoquinone and glycine in a range of mole ratios glycine:benzoquinone of from 1 to 10, mono- and disubstituted glycine-quinone derivatives are formed. After contact of the protein and benzoquinone, said reaction conditions do not make it possible to obtain an activated protein capable of reacting in turn with another biological substance. In particular, the Martin Morrison article does not teach that a very high molar excess of benzoquinone based on the protein is critical to obtain an activated protein which is able to react further.

Furthermore these authors operate only at pH 8 and do not mention the possibility of controlling the addition reactions.

The article by Johnny BRANDT et al [Biochimica et Biophysica Acta 386 (1975) 196–202] bearing the title "Covalent attachment of proteins to polysaccharide carriers by means of benzoquinone" describes the attachment of proteins to solid polysaccharide substrates by means of covalent bonds through the use of benzoquinone as a coupling agent. The authors use agarose and dextran gels which react with benzoquinone in the heterogenous phase, the gels being in a solid state in a buffer medium and being contacted with a benzoquinone solution. Similarly, activated gels are put in suspension in a buffer medium for the coupling reaction, following which the protein is attached to the gel in a covalent manner. Furthermore, J. Brandt et al propose a reactional coupling mechanism.

It should first be noted that the article by Brandt et al relates to a process using an insoluble substrate. The protein is attached to the gel, such as dextrin, the process being especially intended to thus insolubilize the protein. According to the present invention, on the contrary, the activation reactions are conducted in the liquid phase under controlled conditions in order to subsequently permit qualitative and/or quantitative measurements and determinations in the liquid phase. For example, for titering antibodies and antigens by hemolysis, advantage is taken of the property of red blood cells to undergo hemolysis resulting in coloration of the liquid titering medium. Said titering technique is made possible owing to the fact that the reaction products are capable of being used in the liquid phase. The solid substrates of protein-bearing polysaccharides, such as defined by J. Brandt et al, are completely unsuitable for such titering.

There may also be mentioned, as an example of references illustrating the prior art, French patent published under number 2,107,801 owned by the assignee of the present application; said patent which is the certificate of addition n° 70,33,059 solely describes a cross-linking process which results in the insolubilization of biological substances. It consists in forming pores in the cross-linked product formed, in forming or introducing a gas therein, or again by removing a solvent or the reaction mixture during or after cross-linking. Such a process therefore results in a cross-linked product formed of cross-linked or polymerized molecules. It should be emphasized that the invention, on the other hand, retains the solubility of the coupled biological substances in a physiological medium.

Another known process is described in U.S. Pat. No. 3,322,634. It consists in a treatment of red blood cells previously contacted with an aldehyde such as formaldehyde, in the presence of antigens, said process being solely intended to permit hemagglutination of the red blood cells so treated. Such a treatment causes the red blood cells to lose their capacity to lyse. The red blood cells are then placed in a medium containing a phenol or a quinone having a molecular weight lower than 200, and it is only afterwards that attachment is effected with an antigen such as HCG. The process of U.S. Pat. No. 3,322,634 uses red blood cells able to sedimentate and is not put into effect in a homogeneous liquid medium.

Furthermore, according to the invention, the molecules to be coupled are activated prior to their attachment to the red blood cells. This has the advantage, in the case of red blood cells, of making it possible to obtain hemolysis reactions, the applications of which are wider and different from hemagglutination tests. An important characteristic of the invention is that the substances to be coupled are first treated with benzoquinone and then added to the untreated red blood cells, thanks to which the red blood cells retain lyse properties. The benzoquinone to a large extent preserves the activity of the various molecules and hemolysis reactions are made possible by the use of the normal saline medium in which the reaction takes place. Example 6Ba hereinbelow illustrates the fact that hemolysis tests have a greater sensitivity than agglutination tests.

Example 6Bc below shows a mode of embodiment of the invention which would be impossible to put into effect if the red blood cells were treated with an agent such as formaldehyde.

It will also be observed that the use of benzoquinone as coupling agent permits much more flexible and broader applications than the known coupling agent such as glutaraldehyde. A man of the art knows that when glutaraldehyde is used to couple various proteins the reaction has to be very carefully controlled and this is difficult and sometimes even impossible. In particular the duration of the reaction, the pH glutaraldehyde concentration, glutaraldehyde:protein molar ratios etc have to be chosen so that the activation reaction does not extend beyond certain limits, failing which, in extreme cases, the polymerized protein becomes insoluble. It is therefore necessary to adapt the operating conditions of activation by glutaraldehyde to each special case. Particular conditions are necessary for each protein. When a new protein is used numerous preliminary trials must be carried out before finding satisfactory reaction conditions.

Moreover, glutaraldehyde does not permit the activation of biological substances such as polysaccharides and nucleic acids. Its use is limited to free amino acids or substances bearing amino acid groups. Glutaraldehyde is therefore limited in its applications.

Benzoquinone, on the contrary, is a coupling agent acting under controllable conditions that can be generalized. For example, the activation can be made one hour at pH 6 either with proteins, or glycoproteins, or polysaccharides with no risk of formation of polymers. During treatment of proteins, for example, activation always occurs easily as soon as the activation conditions determined by the present invention are observed, with no risk of obtaining undesirable polymers. Furthermore, benzoquinone is a coupling agent possessing qualities of general application.

The invention makes it possible to obtain results it was impossible to obtain up to now, in particular with glutaraldehyde.

For example, an antibody or a Fab antibody fragment may be directly activated with benzoquinone and then fixed by coupling another substance used for labelling and as a titering reagent. Another original application of the invention consists in attaching antibodies to natural red blood cells (i.e. chemically untreated ones), which keep the property of being lysed and which are then capable of detecting the corresponding antigens present, for example, in a liquid sample to be tested. To the applicant's knowledge said application have never been realized in the prior art.

The invention has a very interesting specific application in the determination of antitetanic antibodies and of anti DNA antibodies in human serum.

An application of the invention also has as its object a box or kit for determining antibodies present in a biological liquid comprising the following ingredients.

the red blood cells sensitized to antigen 1, activated by benzoquinone, used to constitute a standard range with the standard antigen and to effect the reaction with the antibodies 1 present in the sample to be tested;
standard antigen 1
a solvent such as physiological salt solution, and
a microslide for titering, the hemolysis test simply being effected by adding a bottle containing the complement to the combination defined hereinabove.

The kit as defined also comes within the scope of the invention.

The following examples are intended to illustrate the invention while in no way limiting its scope.

I—Coupling proteins or glycoproteins with macromolecules.

EXAMPLE 1

The coupling of sheep antibodies anti mouse Ig or their Fab fragment with enzymes, such as peroxidase, glucose oxidase, alkaline phosphatase, lactoperoxidase and $\beta$-galactosidase.

1A. Activation of the protein.

EXAMPLE 1A1

5 mg of peroxidase (or other proteins) were dissolved in 0.8 ml 0.1M pH 8 phosphate buffer. Benzoquinone was added in an amount of 6 mg in 0.2 ml ethanol. The reaction was effected at 22° C. for 20 minutes in the dark. The excess quinone and reaction products were separated from the activated peroxidase on a fine (0.9×5 cm) Sephadex G 25 column, equilibrated with 0.1M sodium bicarbonate.

EXAMPLE 1A2

5 mg of peroxidase (or other proteins) were dissolved in 0.8 ml 0.1M pH 6 of phosphate buffer. Benzoquinone was added in an amount of 6 mg in 0.2 ml ethanol. The reaction was effected at 22° C. for one hour in the dark. The excess quinone and reaction products were separated from the activated peroxidase on a fine (0.9×5 cm) Sephadex G 25 column, equilibrated with 0.1M sodium bicarbonate.

1B Coupling of proteins with one another

EXAMPLE 1B-1

5 mg of peroxidase "activated" in accordance with example 1A2, in 1 ml of 0.1M sodium bicarbonate, were put to couple with 5 mg Fab (or 20 mg antibody) in a 5 mg/ml solution in 0.1M sodium bicarbonate. Coupling was effected for 24 hours at a temperature of less than 22° C. or for 48 hours at 4° C.

Coupling yields showed that about 30% of the Fab was coupled with 30% peroxidase when the proteins were put to react in a mole ratio of 1 to 1, but said rate increased to 65% when 1 molecule of Fab was put to react with 4 molecules of "activated" peroxidase. Under these last conditions, only 35% of the Fab was coupled with the peroxidase if it had been activated with glutaraldehyde.

EXAMPLE 1B-2

5 mg of alkaline phosphatase, "activated" in accordance with example 1A2, was put to couple with 2.5 mg Fab (or 10 mg antibody) under the same conditions as in example 1B-1.

EXAMPLE 1B-3

5 mg of glucose oxidase "activated" in accordance with example 1A2, was put to couple with 1.25 mg Fab (or 5 mg antibody) under the same conditions.

Substantially identical results are obtained if alternatively activation of antibodies is first effected, followed by coupling with the enzyme.

EXAMPLE 1B-4

5 mg of activated antibody or 1,25 mg Fab antibody fragment was put to couple with 5 mg of enzyme which was peroxidase. The yield obtained, i.e. the percentage of activated Fab attached to the enzyme, was practically 75% when the operation was conducted according to the technique described in example 1B-1.

Other tests were conducted under the same conditions with glucose oxidase alkaline phosphatase, β-galactosidase and lactoperoxidase. Similar results were obtained as with peroxidase, in each case using about 4 molecules of enzyme for 1 molecule of activated Fab.

EXAMPLE 1B5

1,25 mg Fab "activated" in accordance with example 1B2 were put to couple with 5 mg Fab anti-peroxidase. In this case, Fab anti-peroxidase can be used as labelling if it is contacting with peroxidase after the coupling reaction Fab-Fab anti-peroxidase with the antigen.

The enzymes and antibodies treated by benzoquinone retained more than 65% of their activity.

The various compositions obtained in example 1 were used successfully to detect immunoglobulines secreted by the lymphoid cells of immunized animals. The technique used was as follows: cells obtained from the spleen or ganglions of mice which had received an injection of antigen a few days previously smeared on a microscope slide, fixed and then incubated with mouse anti Ig Fab fragment coupled with the enzyme. After washing, the enzyme was revealed by its specific cytochemical reaction. The coloration obtained made it possible, with a microscope, to localize the site of the Fab reaction. Using a method of successive dilutions of the Fab coupled with the enzyme, made it possible to compare the activity of said couplings compared with that obtained with glutaraldehyde. The sensitivity of the two reagents at equal concentrations of antibodies were identical. Taling into account the rate of coupling obtained it is seen that the process of the invention is superior to the known process using glutaraldehyde.

II. Coupling polysaccharides with macromolecules in a homogeneous liquid medium.

EXAMPLES 2 and 3

Coupling Salmonella typhi polysaccharide T with enzymes.

EXAMPLE 2

This example illustrates the coupling involving activation of the polysaccharide.

2A Activation of the polysaccharide 1 mg of polysaccharide T was dissolved in 0.8 ml 0.1M pH 6 phosphate buffer. Benzoquinone was added at a rate of 6 mg in 0.2 ml ethanol. The reaction was effected at 22° C. for 1 hour in the dark. The excess of quinone and reaction products were separated from the "activated" polysaccharide by filtration on Sephadex as in example 1A2.

2B Coupling of polysaccharide T with the enzyme 1 mg of polysaccharide T "activated" in 1 ml of 0.1M sodium bicarbonate was put to couple with 2 mg of alkaline phosphatase (or another enzyme) in 0.2 ml 0.1M sodium bicarbonate. Coupling was effected for 24 hours at room temperature.

EXAMPLE 3

Coupling by the enzyme activation method.

3A Activation of the enzyme

The operation was conducted in the same manner as in example 1A2 using an enzyme selected from peroxidase, alkaline phosphatase and glucose oxidase.

3B Coupling an enzyme with polysaccharide 1 mg of enzyme "activated" according to example 3A in 0.2 ml of 0.1M sodium bicarbonate was put to couple with 1 mg polysaccharide in 0.1 ml 0.1M sodium bicarbonate. Coupling was effected for 24 hours at room temperature.

III. Coupling nucleic acids with macromolecules

EXAMPLES 4 and 5

Coupling DNA with an enzyme.

EXAMPLE 4

Coupling by the DNA activation method.

4A Activation of DNA 1 mg of DNA was dissolved in 0.7 ml 0.1M pH 6 phosphate buffer. Benzoquinone was added at a rate of 6 mg in 0.2 ml ethanol. The reaction was effected at 22° C. for 1 hour in the dark. The mixture was filtered through Sephadex as in example 1A.

4B Coupling "activated" DNA and peroxidase 1 mg of DNA "activated" in 1 ml of 0.1M pH 8 phosphate buffer was put to couple with 1 mg peroxidase in 0.1 ml 0.1M pH 8 phosphate buffer. Coupling was effected for 24 hours at room temperature.

EXAMPLE 5

Coupling by the enzyme activation method.

5A Activation of the enzyme

The operation was conducted in the same manner as in example 1A2 using an enzyme selected from peroxidase, alkaline phosphatase and glucose oxidase.

5B. Coupling the enzyme with DNA 1 mg of enzyme, "activated" according to example 5A in 0.2 ml 0.1M phosphate was put to couple with 1 mg ADN in solution in 0.1M pH 8 phosphate buffer.

IV. Coupling macromolecules with red blood cells

EXAMPLE 6

The process of the invention was applied to the coupling of activated proteins, glycoproteins and polysaccharides with red blood cells with the aim of carrying out hemagglutination or hemolysis reactions.

6A. Activation of proteins or polysaccharide.

Said activation and filtration on Sephadex were effected as previously described in example 1A1.

6B Coupling macromolecules with red blood cells 0.25 ml of a bottom of washed red blood cells was added to 1 mg of proteins or polysaccharides "activated" according to example 6A in 1 ml of 0.1M sodium bicarbonate. After 2 hours stirring at room temperature the red blood cells were washed 3 times in the medium which will be used for the hemagglutination or hemolysis reaction.

The various preparations were used to detect both the presence of antibodies or antigens in biological fluids and cellular secretion, by suitable methods.

(a) Determination of antibodies by hemagglutination or hemolysis

Example: determination of antitetanic antibodies in human serum.

The antiserum to be filtered was diluted in a successive manner volume by volume (0.05 ml) in a buffer containing $Mg^{+++}$ and $Ca^{+++}$ (necessary for the hemolysis reaction). The red blood cells sensitized with the tetanic toxin by benzoquinone were added (0.01 ml of a 5% solution) and the vats were agitated to put the red blood cells into suspension. After 45 minutes at 37° C., the hemagglutination reaction was very visible. Then, if the complement is added, hemolysis of the red blood cells occurs 45 to 60 minutes later at 37° C. Generally speaking, lysis of red blood cells is visible at least 2 dilutions after agglutination.

(b) antigen titering by hemagglutination or hemolysis

Example: determination of IgG in mouse serum.

The mouse serum is diluted in the same way as the antiserum in example (a). The red blood cells sensitized with the antibody or the Fab fragment of the antibody were added as in example (a). After 45 minutes at 37° C., the agglutination reaction was visible. Hemolysis was conducted by the addition of the complement as in example (a).

(c) Detection of protein secretion by cells by the local hemolysis technique

Example: detection of the secretion of antibodies by immunocytes. The local hemolysis reaction was effected according to conventional hemolysis techniques either in a gel or in liquid phase, with cells obtained from the sphen or ganglions of immunized animals, and the red blood cells were sensitized with either proteins, glycoproteins or polysaccharides.

To demonstrate the degree of benzoqinone concentration during the activation reaction, trials were conducted including activating the peroxidase by benzoquinone under otherwise identical conditions but with different amounts of benzoquinone in each case. The results obtained were demonstrated by fixing the activated peroxidase on red blood cells and effecting hemolysis. Hemolysis is a convenient means for showing the yield of the reaction. The absence of hemolysis indicates that fixing has not occurred. The degree of hemolysis makes it possible to estimate qualitatively the yield of the reaction.

The reaction conditions were identical to those of example 1A1. The amount of peroxidase put to react was 5 mg. The variable amounts of benzoquinone were dissolved each time in 0.2 ml ethanol. The results are given in the following table.

TABLE

| Peroxidase (amount) | 5 mg | 5 mg | 5 mg |
|---|---|---|---|
| Benzoquinone (amount) | 6 mg | 0,6 mg | 0,06 mg |
| Hemolysis | 100% | 25% | no hemolysis |

The above results show the determinant influence of the concentration of benzoquinone on the reaction yield.

The invention is in no way limited to the example of application given above as illustrations. They relate to a general means for coupling biological substances by using benzoquinone.

V. In situ labelling of cell like constituents using benzoquinone conjugated Fab The principle is as follows: Fab previously coupled with benzoquinone acts on anantigen containing support with reaction conditions antigen-antibody at pH 6,5. After having removed the excess of Fab, the pH is elevated at 8, activating then the free quinone group. If the amino groups of the support are blocked the benzoquinone will react with those of the labelling substance added in the alkaline medium.

EXAMPLE 7

7A Fab activation

This activation and the filtration on Sephadex has been effected like described above in example 1A2.

7B. In situ labelling:

The cells fixed in formol are incubated in a Fab solution (0.5-1 mg/ml in 0,15M NaCl) for one hour. After washing in 0.15M NaCl, the cells are incubated in a peroxidase solution (or a solution of another labelling substance) in 0.1M sodium bicarbonate for at least 6 hours.

We claim:

1. The product of coupling two biological substances by covalent bonds by the steps of
   (a) mixing a first substance dissolved in solution by at least about 200 times its molar amount of benzoquinone in a homogeneous liquid medium to activate said first substance, said first substance being selected from the group consisting of proteins, glycoproteins, polysaccharides and nucleic acids,
   (b) removing the reaction products of step (a) and the excess benzoquinones and recovering the activated first substance; and
   (c) contacting the activated first substance with the second substance to be coupled, said second substance being selected from the group consisting of proteins, glycoproteins, polysaccharides, nucleic acids and red blood cells, the product retaining a large proportion of the biological activities of the first and second substance.

* * * * *